(12) United States Patent
Haaber et al.

(10) Patent No.: US 12,193,975 B2
(45) Date of Patent: Jan. 14, 2025

(54) USER-CUSTOMISED GOGGLES

(71) Applicant: THEMAGIC5 INC., Charlotte, NC (US)

(72) Inventors: Bo Haaber, Birkerød (DK); Anders Dalsgaard, Birkerød (DK)

(73) Assignee: THEMAGIC5 INC., Charlotte, NC (US)

( * ) Notice: Subject to any disclaimer, the term of this patent is extended or adjusted under 35 U.S.C. 154(b) by 0 days.

(21) Appl. No.: 18/510,057

(22) Filed: Nov. 15, 2023

(65) Prior Publication Data

US 2024/0082061 A1  Mar. 14, 2024

Related U.S. Application Data

(63) Continuation of application No. 16/349,069, filed as application No. PCT/EP2017/079178 on Nov. 14, 2017, now Pat. No. 11,857,464.

(30) Foreign Application Priority Data

Nov. 14, 2016 (DK) .......................... PA 2016 70904

(51) Int. Cl.
  *A61F 9/02* (2006.01)
  *A63B 33/00* (2006.01)
  (Continued)

(52) U.S. Cl.
  CPC ............ *A61F 9/026* (2013.01); *A63B 33/004* (2020.08); *G02C 11/12* (2013.01); *G02C 13/003* (2013.01); *B33Y 80/00* (2014.12); *G02C 5/00* (2013.01)

(58) Field of Classification Search
  CPC ....... A61F 9/026; A63B 33/004; G02C 11/12; G02C 13/003; G02C 5/00; B33Y 80/00
  (Continued)

(56) References Cited

U.S. PATENT DOCUMENTS 5,727,259 A * 3/1998 Kawamata ......... A44B 11/2592
  2/452
6,349,417 B1 * 2/2002 Chiang ................ A63B 33/008
  2/445

(Continued)

FOREIGN PATENT DOCUMENTS

DE  201 13 478 U1  2/2002
EP  1 857 150 A2  11/2007
(Continued)

OTHER PUBLICATIONS

PCT/EP2017/079178, International Search Report issued on Mar. 8, 2018.

(Continued)

*Primary Examiner* — Sharrief I Broome
(74) *Attorney, Agent, or Firm* — Meunier Carlin & Curfman LLC

(57) ABSTRACT

The present application relates to a method of identifying data for producing user-customised goggles, which contacts the face of the user defined by a contacting surface on said face, when the user uses said goggles, the method comprising the steps of, receiving an input of 3D-data defining the contour of the face of the user and defining the dimension of the face of the user at least in an area around the eyes of the user, identifying contact areas on the contacting surface, and providing structure-data based on said input of 3D-data and said contact areas, where the structure-data is used for designing at least the part of said goggles, which is adapted to contact the face of the user. The application further relates to a system for producing a pair of user-customised goggles, a pair of user-customised goggles, and a user contacting structure of a pair of user-customised goggles.

10 Claims, 7 Drawing Sheets

(51) Int. Cl.
*B33Y 80/00* (2015.01)
*G02C 5/00* (2006.01)
*G02C 11/00* (2006.01)
*G02C 13/00* (2006.01)

(58) Field of Classification Search
USPC .................................................. 2/428; 703/1
See application file for complete search history.

(56) References Cited

U.S. PATENT DOCUMENTS

| | | | |
|---|---|---|---|
| 6,349,420 B1* | 2/2002 | Chiang | A63B 33/004 2/441 |
| 6,405,384 B1* | 6/2002 | Chiang | A63B 33/004 2/428 |
| D867,438 S | 11/2019 | Haaber | |
| 2006/0219246 A1 | 10/2006 | Dennis | |
| 2008/0263753 A1* | 10/2008 | Chiang | A63B 33/004 2/431 |
| 2010/0313339 A1 | 12/2010 | Chou | |
| 2012/0255104 A1* | 10/2012 | Didier | A61F 9/025 2/426 |
| 2013/0174333 A1* | 7/2013 | Schwartz | A61F 13/043 2/446 |
| 2014/0043329 A1 | 2/2014 | Wang et al. | |
| 2014/0189944 A1* | 7/2014 | Lynd | A63B 33/004 2/452 |
| 2015/0055085 A1 | 2/2015 | Fonte et al. | |
| 2015/0157822 A1 | 6/2015 | Karpas et al. | |
| 2015/0212343 A1* | 7/2015 | Fonte | A61B 3/111 700/98 |
| 2015/0273170 A1* | 10/2015 | Bachelder | A61M 16/0611 264/129 |
| 2015/0351964 A1* | 12/2015 | Schwartz | A61F 9/029 2/440 |
| 2016/0103335 A1* | 4/2016 | Ben-Shahar | G02C 7/027 351/159.01 |
| 2018/0296783 A1 | 10/2018 | Davis | |
| 2019/0369418 A1 | 12/2019 | Joy et al. | |

FOREIGN PATENT DOCUMENTS

| | | | |
|---|---|---|---|
| FR | 2 937 558 A1 | 4/2010 | |
| WO | WO-2016176630 A1 * | 11/2016 | ............. B29D 12/02 |
| WO | 2018087386 A1 | 5/2018 | |

OTHER PUBLICATIONS

PCT/EP2017/079178, PCT Written Opinion of ISA issued on Mar. 8, 2018.
Office Action in connection to EP Application No. 17807747.5, dated Oct. 28, 2022.
International search report and written opinion in PCT/US2021/026863. Mailed Jul. 27, 2021. 12 pages.
Custom Fitted Goggles, posted at swimswam.com, posting date Oct. 6, 2017, [online], [site visited Nov. 4. 2022]. Available from Internet , URL: https://swimswam.com/the-worlds-first-custom-fitted-goggles-kickstarter/ (Year: 2017).

* cited by examiner

USER-CUSTOMISED GOGGLES

This application is a continuation of U.S. application Ser. No. 16/349,069 filed May 10, 2019, which is a 371 of international application number PCT/EP2017/079178 filed Nov. 14, 2017, which claims priority to and benefit of Denmark (DK) application PA201670904 filed Nov. 14, 2016, each of which are fully incorporated by reference and made a part hereof.

The present invention relates to a method of identifying data for producing user-customised goggles, which contacts the face of the user defined by a contacting surface on said face, when the user uses said goggles, the method comprising the steps of
  receiving an input of 3D-data defining the contour of the face of the user and defining the dimension of the face of the user at least in an area around the eyes of the user,
  identifying contact areas on the contacting surface,
  providing structure-data based on said input of 3D-data and said contact areas, where the structure-data is used for designing at least the part of said goggles, which is adapted to contact the face of the user.

The invention further relates to a system for producing a pair of user-customised goggles, a pair of user-customised goggles, and a user contacting structure of a pair of user-customised goggles.

Most people have at one time worn a pair of goggles (or safety glasses) as a shield (or protective eyewear) for protecting the eyes from e.g. glare, dust, water, etc. The required degree of close-fit between the goggles and the face of the user depends on the intended use, however in all cases it may be difficult to find an acceptable combination of a sufficiently close-fitting and comfortable pair of goggles, as inter alia the contour and size of the human face and the location of the eyes relative to each other varies from person to person.

In case the pair of goggles is a pair of swimming goggles, the search for an acceptable pair of goggles can be time-consuming and costly. If the goggles are not sufficiently comfortable, the result may be that the user interrupts the swimming session several times in order to adjust the goggles and therefore will not have an optimal swimming session. If the goggles are not sufficiently close-fitting on the face, the user will get water in the eyes resulting in discomfort or an interruption of the swimming session. To prevent getting water in the eyes, the user may use a pair of too large goggles, or may tighten the goggles too must around the eyes, which may be painful. Often the problem is that the goggles do not fit perfectly with the contour of the face around the eyes.

Thus, known goggles do not provide a combination of a sufficiently close-fitting and comfortable pair of goggles.

In accordance with the invention, there is provided a method of identifying data for producing user-customised goggles, which contacts the face of the user defined by a contacting surface on said face, when the user uses said goggles, the method comprising the steps of
  receiving an input of 3D-data defining the contour of the face of the user and defining the dimension of the face of the user at least in an area around the eyes of the user,
  identifying contact areas on the contacting surface,
  providing structure-data based on said input of 3D-data and said contact areas, where the structure-data is used for designing at least the part of said goggles, which is adapted to contact the face of the user.

Providing user-customised goggles is advantageous, as it is ensured that the goggles fit perfectly (have an optimal position) on the face of the user. Further, the risk of the user having to wear uncomfortable goggles that may hurt, or the risk of a leak of e.g. water entering the eyes of the user when wearing the goggles, is minimised.

By providing user-customised goggles based on 3D-data defining the contour of the face of the user and defining the dimension of the face of the user at least in an area around the eyes of the user, it is ensured that the goggles are designed based on the real contour of the face of the user. The goggles are not designed based on just an estimate of how the contour of a face would generally look like combined with a flexible membrane to compensate for not-similar areas between the face of the user and said goggles. An area around the eyes of the user may comprise at least the area, i.e. the contacting surface, intended for being in contact with said goggles, when the user wears said goggles, which area may vary depending on the type of goggles. Thus, the user-customised goggles may be based on the contour of the region around the eyes of the user, and may thereby be based without focusing on e.g. the region around the nose and the width of the face.

By providing structure-data based on said input of 3D-data and said contact areas, where the structure-data is used for designing at least the part of said goggles, which is adapted to contact the face of the user, the contour of said part of said goggles is therefore designed to follow the contour of the face of the user, around at least one of the eyes of the user.

Within the present application, goggles may be understood as an element, which is adapted to encircle at least one of the eyes of the user. Thus, goggles may encircle the eyes of the user one by one or may encircle both of the eyes together, such as may be the case for swimming goggles or diving goggles, respectively. The goggles may shield or completely seal the eyes from the surroundings depending on the type and use of goggles, and may as such be used for swimming, working with power tools or welding, laboratory work, etc., and may be used as ski goggles, (fire)-fighting goggles, gasmasks, etc.

Within the present application, a contacting surface may be understood as an area or line on the face of the user, which at least partly surrounds/encircles the eyes of the user. Therefore, the contacting surface may be one area or line that sur-rounds/encircles both eyes, or may be two areas or lines each of which sur-rounds/encircles an eye. Further, the location of the contacting surface on the face of the user may be predefined, however said location may also be determined depending on the contour of the face of the user and/or on contact areas defined by the user. I.e. if the goggles are intended to be of a small size (e.g. swimming goggles), the contacting surface is located close to the eyes of the user compared to if the goggles are intended to be of a large size (e.g. diving goggles), where the contacting surface is located further away from the eyes of the user.

Thus, a perfectly fitting and comfortable pair of goggles are provided.

In an embodiment, an input of said structure-data can be provided to a production unit for producing at least the part of said goggles, which is adapted to contact the face of the user. In an embodiment, an input of said structure-data can be provided to a production unit for producing a form for producing at least the part of said goggles, which is adapted to contact the face of the user.

The production unit may be a 3D-printing unit such as a 3D-printer, which is a well-established and tested means for printing/producing a 3D-element with a complicated structure in a fast and precise manner. Thus, the structure-data may be of a format, which is adapted to be received and read by a 3D-printing unit.

At least the part of said goggles, which is adapted to contact the face of the user (or a form for producing said part) may be produced by the production unit, as said part reproduces the contour of the face of the user at said contacting surface and therefore takes part in customising the goggles to the user. Thus, the entire or only part of the user-customised goggles may be produced by the production unit. If only part of the user-customised goggle is produced by the production unit, then the remainder part of said goggles, such as the goggle frame, may be produced with a predetermined shape. The two parts of said goggles may then be combined after production.

In an embodiment, the method can further comprise providing a plurality of 2D-images of the face of the user, where the 2D-images define the dimension of the face of the user at least in the area around the eyes of the user, and producing said 3D-data based on said plurality of 2D-images.

Producing said 3D-data based on a plurality of 2D-images is advantageous, as well-known techniques exist, which result a reliable reconstruction of the face of the user.

2D-images can be obtained by use of a detection unit. The detection unit may be an optical detection unit such a camera or a smartphone. Optical detection units are known to give a reliable and high quality image and is today found in a lot of electronic devices such as in mobile phones or tablets.

In an embodiment, identifying contact areas can comprise defining at least one point on each wanted contacting surface on the face of the user. The contact areas may form the basis for determining the shape of the contacting surface on said face.

The defining of at least one point may be done either manually by e.g. marking a data point on said 3D-data or automatically.

In an embodiment, the method can further comprise identifying the edges of the eyes of the user in the 3D-data. Said edges may be the contact points between the upper and lower eye lids of the user. By identifying the edges of the eyes, the contacting surface can more easily be determined as the contacting surface is to encircle, but not touch the eyes of the user.

In accordance with the invention, there is further provided a system for producing a pair of user-customised goggles, which contacts the face of the user defined by a contacting surface on said face, when the user uses said goggles, the system comprising a processing unit being adapted to receive and analyse an input of 3D-data defining the contour of the face of the user and defining the dimension of the face of the user at least in an area around the eyes of the user, and adapted to identify contact areas on the contacting surface, and to provide structure-data based on said input of 3D-data and said contact areas, where the structure-data is used for designing at least the part of said goggles, which is adapted to contact the face of the user, a production unit adapted to receive an input of said structure-data and to produce an element based on said structure-data.

In an embodiment, the contacting surface can be surrounding each of the eyes of the user.

In an embodiment, the production unit can be adapted to produce at least the part of said goggles, which is adapted to contact the face of the user, or to produce a form to produce said part.

In an embodiment, the system can further comprise a detection unit for producing a plurality of 2D-images of the face of the user. The detection unit may be an optical detection unit such a camera or a smartphone. Optical detection units are known to give a reliable and high quality image and is today found in a lot of electronic devices such as in mobile phones or tablets.

The processing unit may automatically carry out these steps of receiving the input of 3D-data, identifying the contact areas on the contacting surface, and providing structure-data. Thereby, the processing unit provides a fast, precise and low cost way of obtaining structure-data.

In an embodiment, the processing unit can further be adapted to receive and analyse a plurality of 2D-images of the face of the user, where the 2D-images defines the dimension of the face of the user at least in the area around the eyes of the user, and adapted to produce said 3D-data based on said plurality of 2D-images.

The process from either receiving 2D-images or 3D-data to providing structure-data and/or producing at least the part of said goggles, which is adapted to contact the face of the user, may be carried out at least partly automatic by the processing unit. Thus, said process may be easily operable for the user, fast and low cost.

In accordance with the invention, there is further provided a pair of user-customised goggles, which contacts the face of the user defined by a contacting surface on said face, when the user uses said goggles, the goggles comprising at least a user contacting part adapted to contact the face of the user, where the user contacting part reproduces the contour and dimension of the face of the user at the contacting surface.

In an embodiment, the contacting surface can be surrounding each of the eyes of the user.

In an embodiment, the user contacting part can comprise a flexible material. Thus, at least part of the user contacting part can comprise a flexible material, which may in-crease the comfort for the user of wearing the goggles, as the user contacting part may compress or expand, when the goggles are mounted on and tightened to the face of the user. Otherwise, the user contacting part may be pressed too far into the skin on the face of the user, which may lead to discomfort. Providing that the user contacting part comprises a flexible material may also facilitate that the inside of the goggles is sealed from the outside of the goggles to prevent dust, water, etc. from entering the eyes of the user.

In an embodiment, said goggles can comprise a goggle frame comprising the user contacting part.

In an embodiment, a membrane comprising a flexible/elastic material can be mounted on the user contacting part. Said membrane can be arranged between the user contacting part and the face of the user, when said goggles is mounted on the face of the user. Thereby, the user contacting part does not need to comprise a flexible material, but can e.g. comprise a ridged material, while the goggles maintain the wanted comfort and sealing function as described in the previous paragraph. Further, as the membrane comprises a flexible material, the effect that the user contacting part reproduces the contour of the face of the user is maintained.

In an embodiment, the user-customised goggles can be a pair of swimming goggles.

In accordance with the invention, there is further provided a user contacting structure of a pair of user-customised goggles, which contacts the face of the user defined by a contacting surface on said face, when the user uses said goggles, the user contacting structure comprises > a first surface comprising a user contacting part adapted to contact the face of the user, where the user contacting part reproduces the contour and dimension of the face of the user at the contacting surface, and
> a second surface.

In an embodiment, the contacting surface can be surrounding each of the eyes of the user.

In an embodiment, the user contacting structure can be adapted to connect to the glasses of said goggles.

In an embodiment, the second surface can be adapted to connect to a goggle frame.

In an embodiment, the goggle frame and the user contacting structure(s) can be produced as one unit so that no following assembly is required.

Thus, the user contacting structure may as such form the basis of said goggles (i.e. form the goggle frame) such that the glasses (e.g. made of a plastic material or a glass material) of said goggles are mounted directly on the user contacting structure. Further, a possible connecting means (e.g. an aperture) configured for connecting to a strap (elastic or flexible, or at least can be manipulated lengthwise) for securing said goggles to the face of the user can be attached to the user contacting structure and a possible connection piece (connecting two user contacting structures across the nose) of said goggles can be attached directly to said goggles.

In an embodiment, the user contacting structure can comprise a flexible material. Hereby, the comfort for the user of wearing said goggles increases, as the user contacting structure may compress or expand, when said goggles are mounted on and tightened to the face of the user. Otherwise, the user contacting structure may be pressed too far into the skin on the face of the user, which may lead to discomfort. Providing that the user contacting structure comprises a flexible material may also facilitate that the inside of said goggles is sealed from the outside of the goggles to prevent dust, water, etc. from entering the eyes of the user. The user contacting structure may comprise a rubber-based material.

In an embodiment, said first and second surfaces can be separated by a separation length. The separation length may be defined by at least a minimum length to ensure that the goggle frame and/or the glasses of the goggles do not come so close to the eyes of the user that the goggles are uncomfortable to wear as e.g. the eyelashes come in contact with the goggles.

In an embodiment, the separation distance can be larger than 4 mm.

In an embodiment, the user contacting part can comprise a flat surface. Hereby, the area of contact between the user-customised goggles and the face of the user is maximised. Further, the user contacting part is pressed against the face of the user with a force, which is distributed equally across the surface of the user contacting part, which results in optimal fit of the pair of user-customised goggles thus preventing water entering the eyes of the user and preventing an uncomfortable pair of goggles that may hurt.

The inventors have found that the user contacting part may advantageously be approximately 4 mm wide.

In an embodiment, the user contacting structure can comprise a rigid material, so that the contour of the user contacting part, which reproduces the contour of the face of the user at the contacting surface, is maintained thereby maintaining a perfect fit of the goggles on the face of the user.

In an embodiment, the user-customised goggles can comprise a heating means. The heating means may be adapted to heat at least part of the glasses of the goggles so that moist is prevented from forming at the (inside of the) glasses, which is an ad-vantage as moist will limit the sight of the user, e.g. when said goggles is a pair of swimming goggles and the user is swimming in water.

The heating means may comprise at least one pair of electrodes (an anode and a cathode), which may be arranged on the goggle frame or on the user contacting structure a distance apart, so that a current may run from one electrode to the other thereby heating the glasses, when the user is swimming in salty water such as in seawater.

The structure of the user-customised goggles and the method of producing the user-customised goggles will be described in more detail below with references to exemplary embodiments shown in the drawings wherein, FIG. 1 shows in a flow diagram an embodiment of a method of producing a pair of user-customised goggles.

Figure 1:
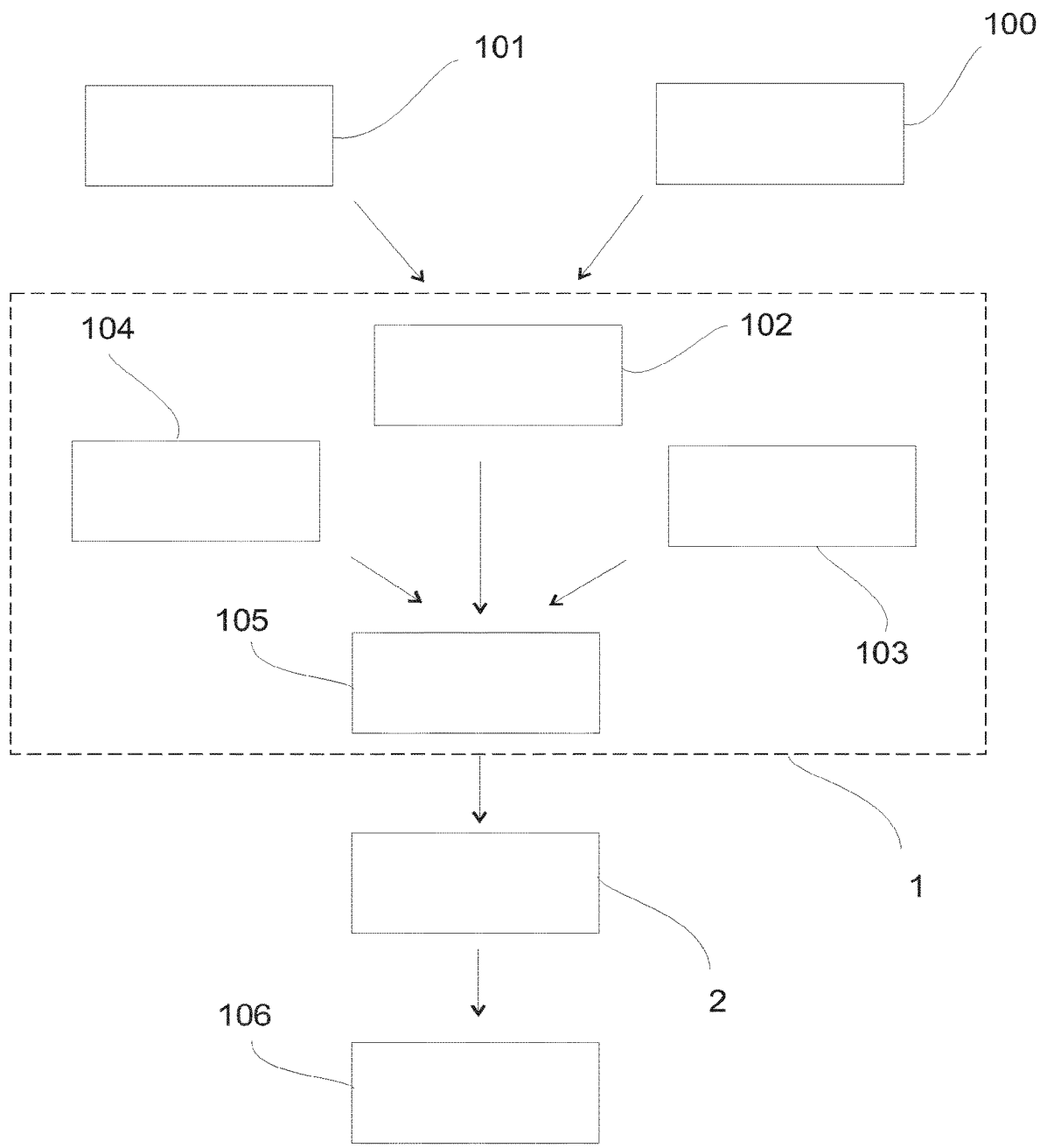

In FIG. 1, a flow diagram is shown of an embodiment of a method of producing a pair of goggles.

In the embodiment of FIG. 1, it is shown that inputs are provided to a processing unit 1. The inputs may comprise a plurality of 2D-images 100 of the face of a user and information regarding the dimension 101 of the face of the user in the 2D-images at least in the area around the eyes of the user. Based on said inputs, the processing unit 1 is adapted to produce 3D-data 102 defining the contour of the face of the user and defining the dimension 101 of the face of the user at least in the area around the eyes of the user.

Alternatively, 3D-data 102 defining the contour of the face of the user and defining the dimension 101 of the face of the user at least in the area around the eyes of the user may be provided directly to the processing unit 1. The 3D-data 102 may comprise a 3D-image and information regarding the dimension of the 3D-image. The 3D-data 102 or 3D-image may e.g. be detected by use of a 3D-camera such as a range camera or a stereo camera.

The 2D-images 100 and/or the 3D-data 102 may be produced/detected by the user e.g. by use of the camera function in the user's smartphone. The production and/or collection and/or transmittal to the processing unit 1 of the 2D-images 100 and/or the 3D-data 102 may be carried out by use of a specially developed application program (app) installed on the user's smartphone or tablet.

The contacting surface 103, which defines the surface on the face of the user intended to contact the goggles, when the user is wearing the goggles, is determined based on the 3D-data 102. Data regarding the contacting surface 103 may be defined automatically by the processing unit 1 based on pre-defined contact areas 104. Alternatively, the processing unit 1 may be provided with information regarding contact areas 104 on the face of the user, where the contacting surface 103 should at least be located, and the processing unit 1 may model the location of the contacting surface 103 based on this information.

The contact areas (facial points) may be identified by use of vectors. Thus, contact areas may be determined based on vectors at points at the eye inner and eye outer corner, and vectors defining the structure change of the face at points going from those locations and away from the eye in a horizontal direction, as well as vectors defining the structure changes of the face at points going from the middle of the eye and a certain distance away from the eye in a vertical direction. The contact areas may be determined this way by vectors not just at a few locations around the eyes, but may be determined at several locations around the eyes so that an optimal contacting surface is obtained.

Thus, as an example, the vertical location of the goggles may be determined (calculated) from vectors at points starting from the middle of the eye and moving up-wards/downwards in the vertical direction. When the vectors reach a predefined angle relative to the face of the user (pointing away from the face), a contacting area on which part of the goggles is to touch the face of the user is located. The horizontal location of the goggles may be determined by use of vectors at points starting from the eye inner corner and going towards and up the nose. When the vectors reach a predefined angle relative to the face of the user, a contacting area on which part of the goggles is to touch the face of the user is located. This technique of determining contact areas may be used at several locations around the eyes so that an optimal contacting surface may be determined and an optimal pair of goggles for the user is produced.

As written above, the contacting surface may also be determined based on only one contact area and a contacting surface of a predefined shape. In this case, the contact area may be determined from vectors at points starting from e.g. the eye inner corner and going towards and up the nose. When the vectors reach a predefined angle relative to the face of the user, a contacting area on which part of the goggles is to touch the face of the user is located.

The optimal contacting surface may be arranged in the vicinity of the edges of the skull of the user, which edges define the eye sockets. Thus, if the position of the contacting surface is altered only slightly (e.g. 2 mm), the contacting surface is possibly not positioned optimally anymore, which may result in that water enters the eyes of the user.

Based on inter alia the provided 3D-data 102 and said contact areas 104, the processing unit 1 may model structure-data 105, which can be used for designing at least the part of said goggles 106, which is adapted to contact the face of the user, i.e. for designing a user contacting part reproducing the contour and dimension of the face of the user at the contacting surface 103.

An input of the structure-data 105 may be provided to a production unit 2 adapted to receive said input of structure-data 105 and to produce at least the part of said goggles 106 (the user contacting part), which is adapted to contact the face of the user, when the user uses/wears the goggles. The production unit 2 may also produce the entire goggles (e.g. the user contacting structure, or the user contacting structure and goggle frame) so that there is no need for assembling the goggle frame and the user contacting part after their production.

An app installed e.g. on the user's smart phone may control the production and/or collection and/or transmittal of the 2D-images 100 and/or the 3D-data 102, however may also carry out the analysis of the 3D-data 102 and provide the structure-data 105. An input of structure-data 105 can then be provided to the processing unit 1 or directly to the production unit 2.

The production unit 2 should be adapted to produce at least part of said goggles 106 based on said structure-data 104 or to produce a form to produce at least said part based on said structure-data 104. The production unit 2 may use one of various techniques such as printing or casting said goggles, or grinding/cutting out said goggles from a base material, etc, automatically or manually. The base material may form at least the part of the goggles, which is adapted to contact the face of the user and may initially be oversized, but during the production be cut such that the goggles fits directly to the skin of the user.

The size of the separation length (e.g. how much of the base material has to be cut off) may inter alia depend on the contour of the face of the user and on how large the root of the nose is.

The applicant has found that the production unit 2 may advantageously be a 3D-printing unit such as a 3D-printer, which is a well-established and tested means for printing a 3D-element with a complicated structure in a fast and precise manner. Today, various types of 3D-printers are commercially available several of which may be applied in the present method depending on inter alia the required material of the part of said goggles to be produced.

Figure 2:
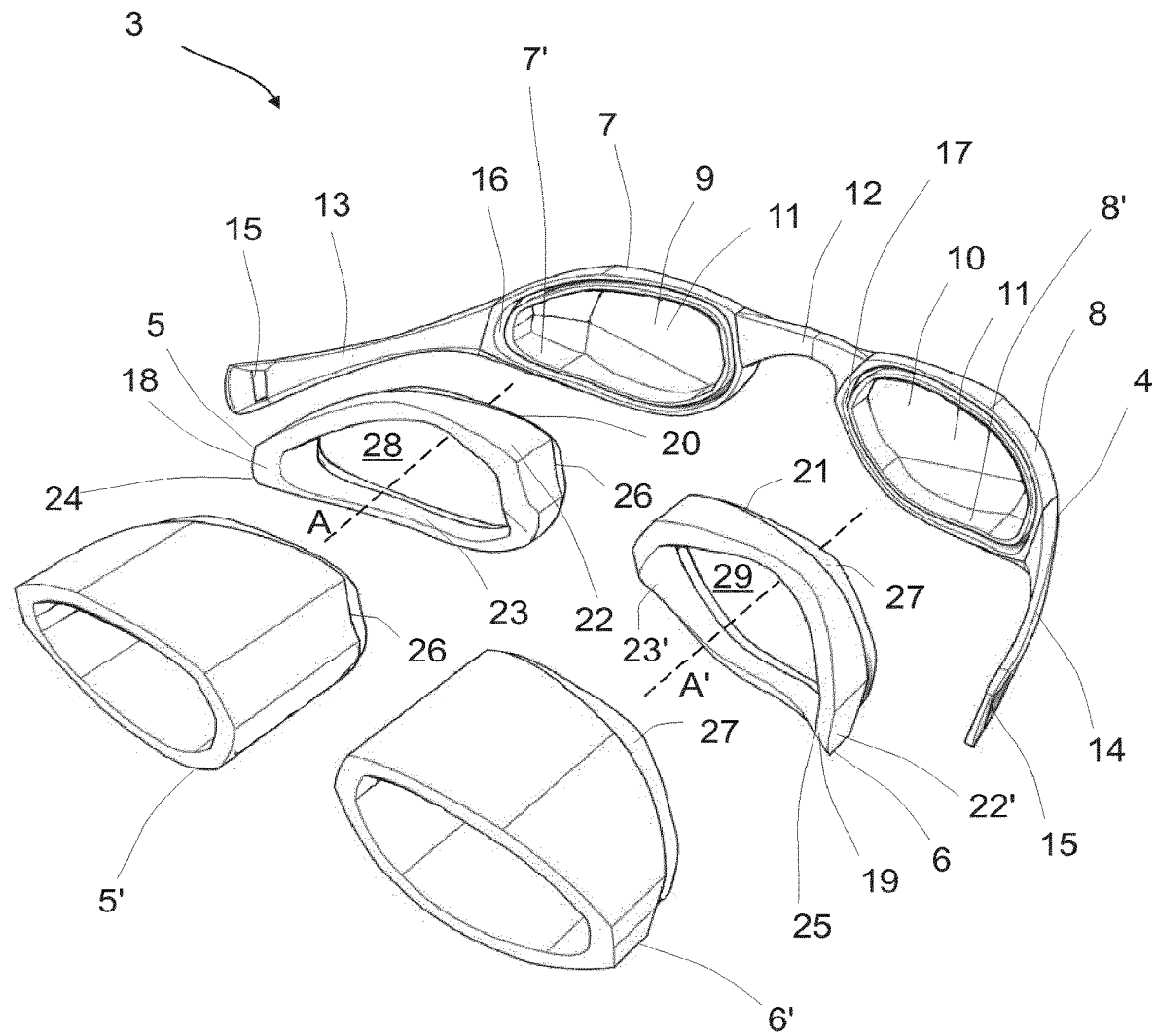
FIG. 2 shows an exploded view of a pair of user-customised goggles, seen in perspective from the back.

In FIG. 2, an exploded view of a pair of user-customised goggles 3 is seen in perspective from the back.

The user-customised goggles 3 may comprise a goggle frame 4 and a user contacting structure, which may comprise a first 5 and a second user contacting structure 6. However, it is foreseen that the goggle frame 4 and the first 5 and second user contacting structures 6 may be produced as one unit.

The goggle frame 4 of FIG. 2 may comprise a first 7 and a second glass or lens frame 8 comprising a first 9 and second opening 10 adapted to accommodate the glasses 11 or lenses 11 of said goggles 3, through which the user can see, when wearing the goggles 3. Each of said first 7 and second glass or lens frame 8 may comprise an inner surface 7', 8', respectively. The first 7 and second glass or lens frame 8 may be connected by a connection piece 12. The goggle frame 4 may further comprise a first 13 and a second side bar 14, each comprising an aperture 15 configured for connecting to an elastic or flexible strap for securing said goggles 3 to the face of the user.

Each of the first 7 and a second glass or lens frame 8 of the goggle frame 4 may comprise a groove 16, 17.

The first 5 and second user contacting structure 6 may comprise a first 18, 19 and a second surface 20, 21, respectively. Said first 18, 19 and second surfaces 20, 21 may be separated by an outer 22, 22' and inner surface 23, 23', respectively, of the first 5 and second user contacting structures 6. Said outer 22, 22' and inner surfaces 23, 23' may be parallel and/or not parallel. Said first 18, 19 and second surfaces 20, 21 may be separated by a separation length (i.e. a width of said outer 22, 22' and/or inner surfaces 23, 23', respectively), which may vary depending on the location on said user contacting structures 5, 6. Thus, the width/thickness of the user contacting structure 5, 6 relative to their central axes A,A' may vary.

The first surfaces 18, 19 of said user contacting structures 5, 6 may each comprise a user contacting part 24, 25 adapted to contact the face of the user, where the user contacting part 24, 25 reproduces the contour and dimension of the face of the user at the contacting surface on the face of the user. Thus, the shape and the size of said user contacting part 24 of said first user contacting structure 5 may be different from said user contacting part 25 of said second user contacting structure 6, and the shape and size of said user contacting parts 24, 25 may each vary from user to user, as the contour of the face varies from user to user. Said user contacting parts 24, 25 may comprise a membrane comprising a flexible material arranged at said first surfaces 18, 19 to contact the skin of the face of the user, when the user wears the goggles. The membrane ensures a comfortable and sealing fit between the face of the user and said goggles.

The second surfaces 20, 21 of said user contacting structures 5, 6 may each comprise a ridge 26, 27 adapted to engage with the grooves 16, 17 of the first 7 and second glass or lens frames 8 of the goggle frame 4 so that a solid and leak free connection is provided between the user contacting structures 5, 6 and the goggle frame 4. Other types of engagement means such as broken grooves/ridges, protrusions/recesses, adhesives, etc. are foreseen within the present application.

The first 5 and second user contacting structures 6 may each comprise an inner opening 28, 29 through which the user can see, when wearing the goggles 3.

In FIG. 2, an examples is shown of the first 5 and second user contacting structures 6 prior to the shaping the first surfaces 18, 19 of the first 5 and second user contacting structures 6 (referred to as 5' and 6', respectively).

Figure 3:
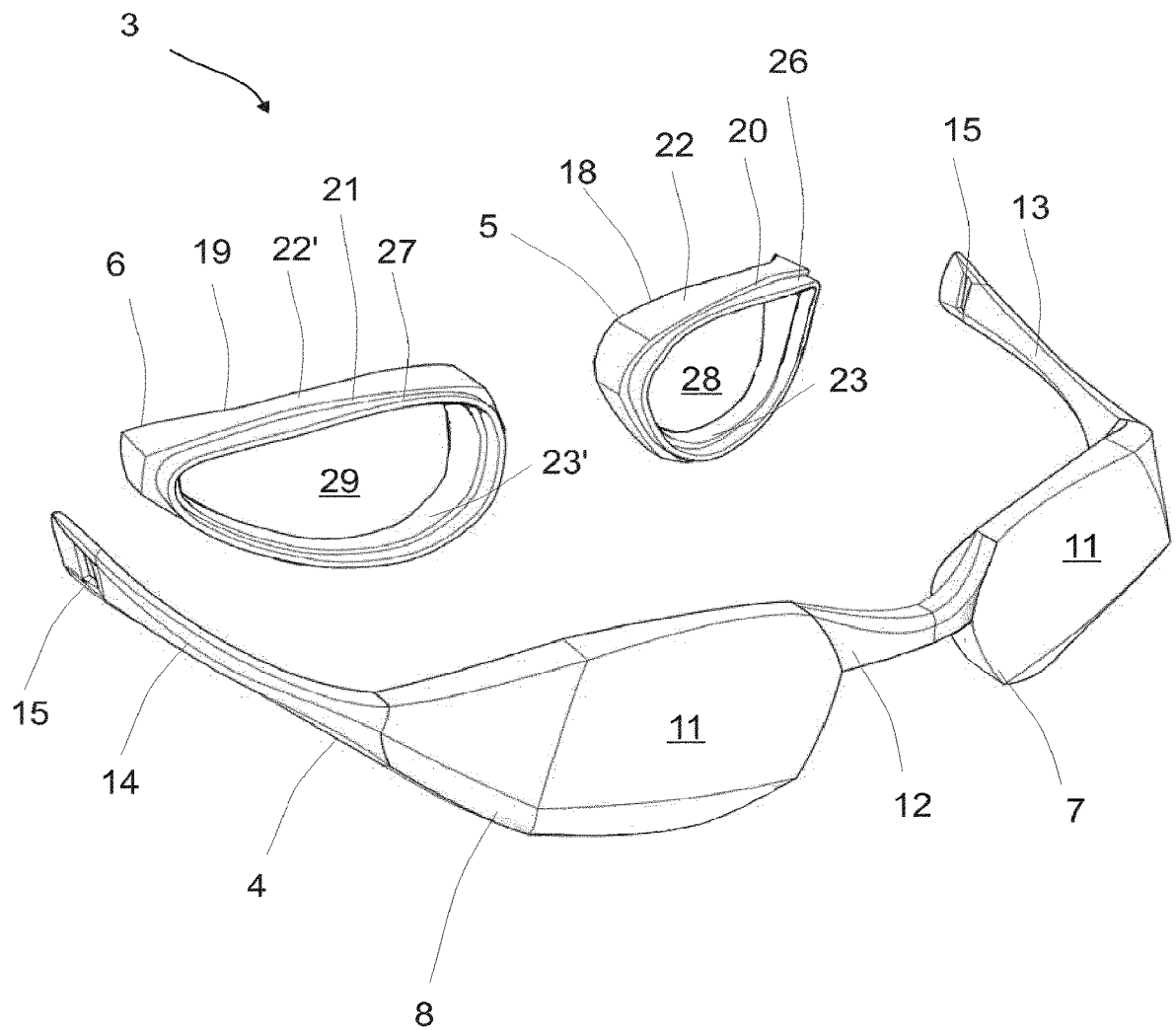
FIG. 3 shows an exploded view of a pair of user-customised goggles, seen in perspective from the front.

In FIG. 3, an exploded view of a pair of user-customised goggles 3 is seen in perspective from the front. For similar features as shown in the previous Figs., similar reference numbers have been used.

In FIG. 3, the goggle frame 4 is shown to comprise said glasses 11 or lenses 11 of said goggles 3, where said glasses 11 or lenses 11 of the goggles 3 may be transparent, so that the user may see through the said glasses 11 or lenses 11, when wearing said goggles 3.

In FIG. 3, it is shown that the second surfaces 20, 21 of the first 5 and second user contacting structures 6 may each comprise the ridge 26, 27 adapted to engage with the grooves 16, 17 (not shown) of the first 7 and second glass or lens frames 8 of the goggle frame 4. Thereby, a solid and leak free connection is provided. The engagement may include a sealant, such as a flexible gasket, arranged between said ridges 26, 27 and said grooves 16, 17, and/or the engagement may include an adhesive, such as a glue or paste, arranged between said ridges 26, 27 and said grooves 16, 17.

Figure 4:
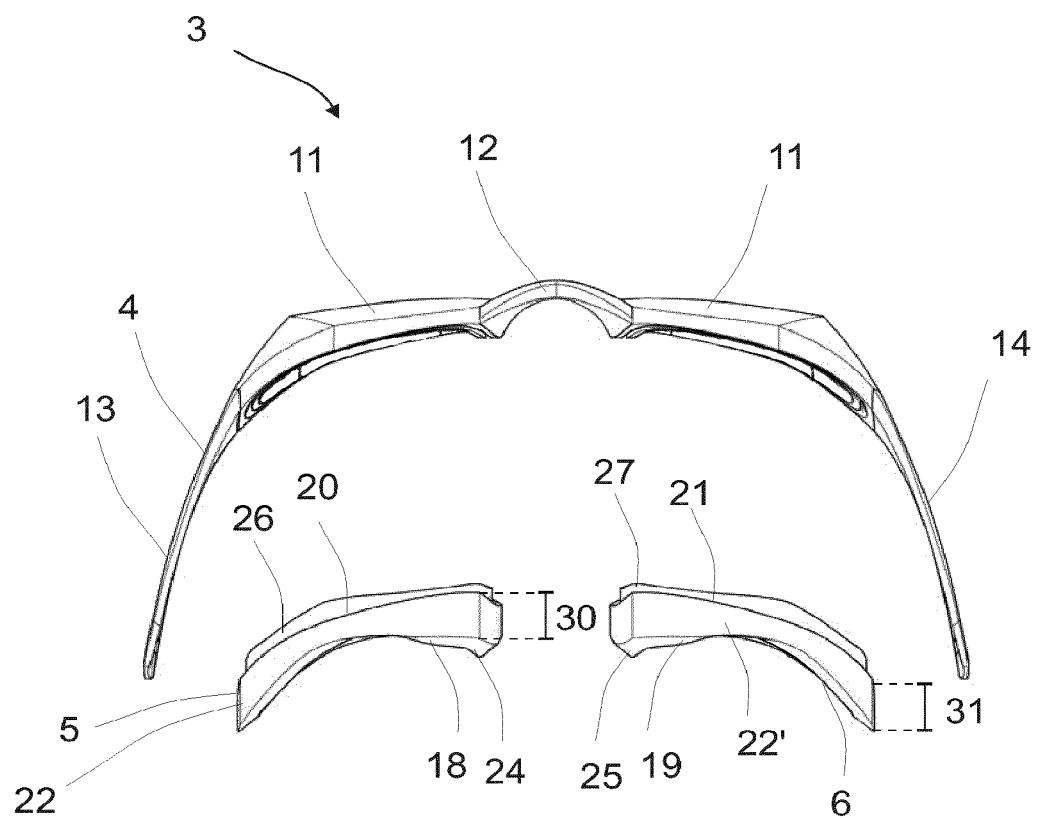
FIG. 4 shows an exploded view of a pair of user-customised goggles, seen from above.

In FIG. 4, an exploded view of a pair of user-customised goggles 3 is seen from above. For similar features as shown in the previous Figs., similar reference numbers have been used.

The first 18, 19 and second surfaces 20, 21 of the first 5 and second user contacting structures 6 are shown to be separated by inter alia said outer surfaces 22, 22' defined by a separation length 30, 31, respectively, which as shown may vary across said outer surfaces 22, 22' of said first 5 and second user contacting structures 6, and which may depend on the contour of the face of the user on the contacting surface on the face of the user surrounding the eyes of the user.

It is seen that said first surfaces 18, 19 of the first 5 and second user contacting structures 6 may have a varying gradient and a varying course relative to said inner 23, 23' and outer surfaces 22, 22' (and the central axes A,A') of the first 5 and second user contacting structures 6, as said first surfaces 18, 19 (and said user contacting parts 24, 25) reproduces the contour of the face of the user.

Figure 5:
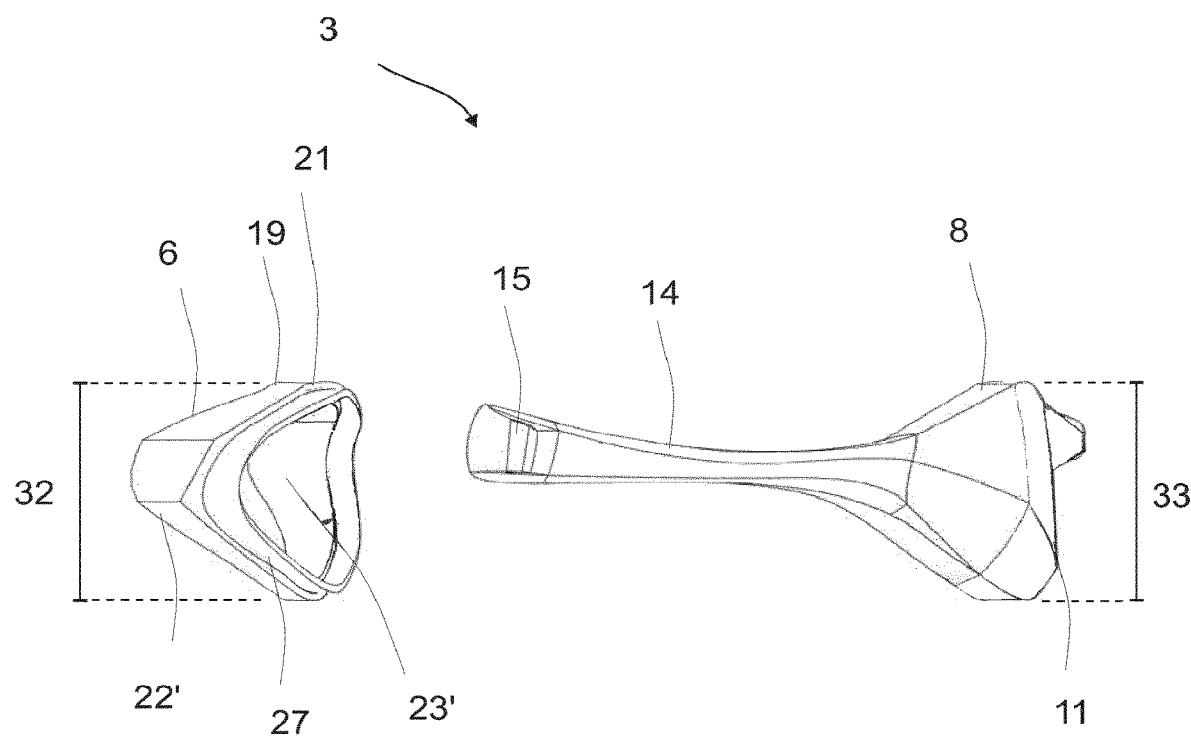
FIG. 5 shows an exploded view of a pair of user-customised goggles, seen from the side.

In FIG. 5, an exploded view of a pair of user-customised goggles 3 is seen from the side. For similar features as shown in the previous Figs., similar reference numbers have been used.

The height 32 of said first 5 and/or second user contacting structure 6 may be similar or different from the height 33 of the goggle frame 4 depending inter alia on the chosen contacting surface on the face of the user and on the type of goggle, e.g. swimming goggles or diving goggles.

Figure 6:
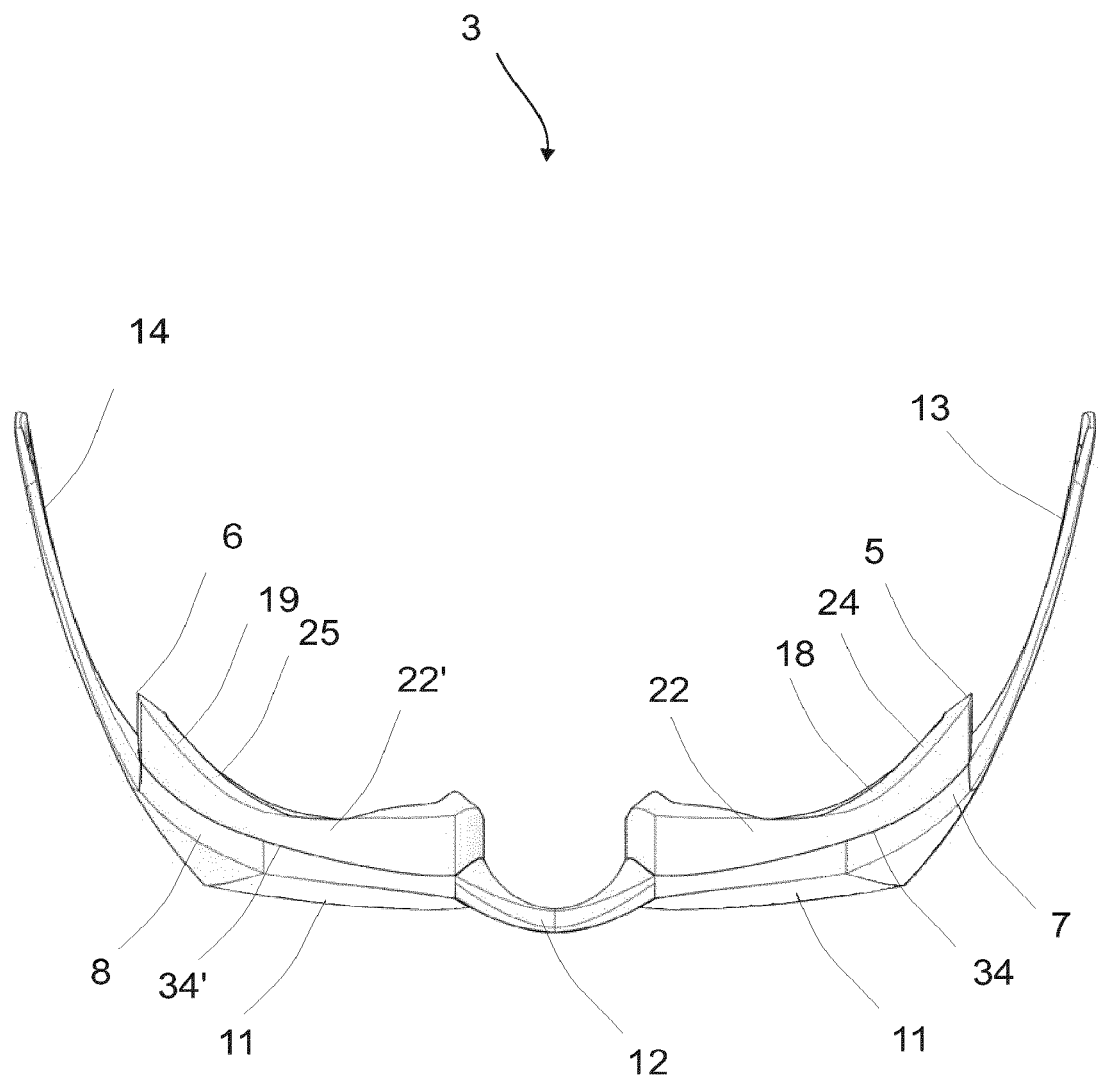
FIG. 6 shows a pair of assembled user-customised goggles, seen from above.

In FIG. 6, a pair of assembled user-customised goggles 3 is seen from above. For similar features as shown in the previous Figs., similar reference numbers have been used.

It is shown that the first 5 and/or second user contacting structures 6 may protrude at least partly out from a back side 34, 34' of said goggles 3 so that at least the user contacting parts 24, 25 of the first surfaces 18, 19 of said user contacting structures 5, 6 is adapted to contact the face of the user, when the user wears said goggles 3. Alternatively, only said first surfaces 18, 19 protrude from the back side 34, 34' of said goggles 3 so that the goggle frame 4 encircles the outer surfaces 22, 22' of said user contacting structures 5, 6.

The goggle frame 4 and the user contacting structures 5, 6 may be produced as one unit so that no following assembly is required.

Figure 7:
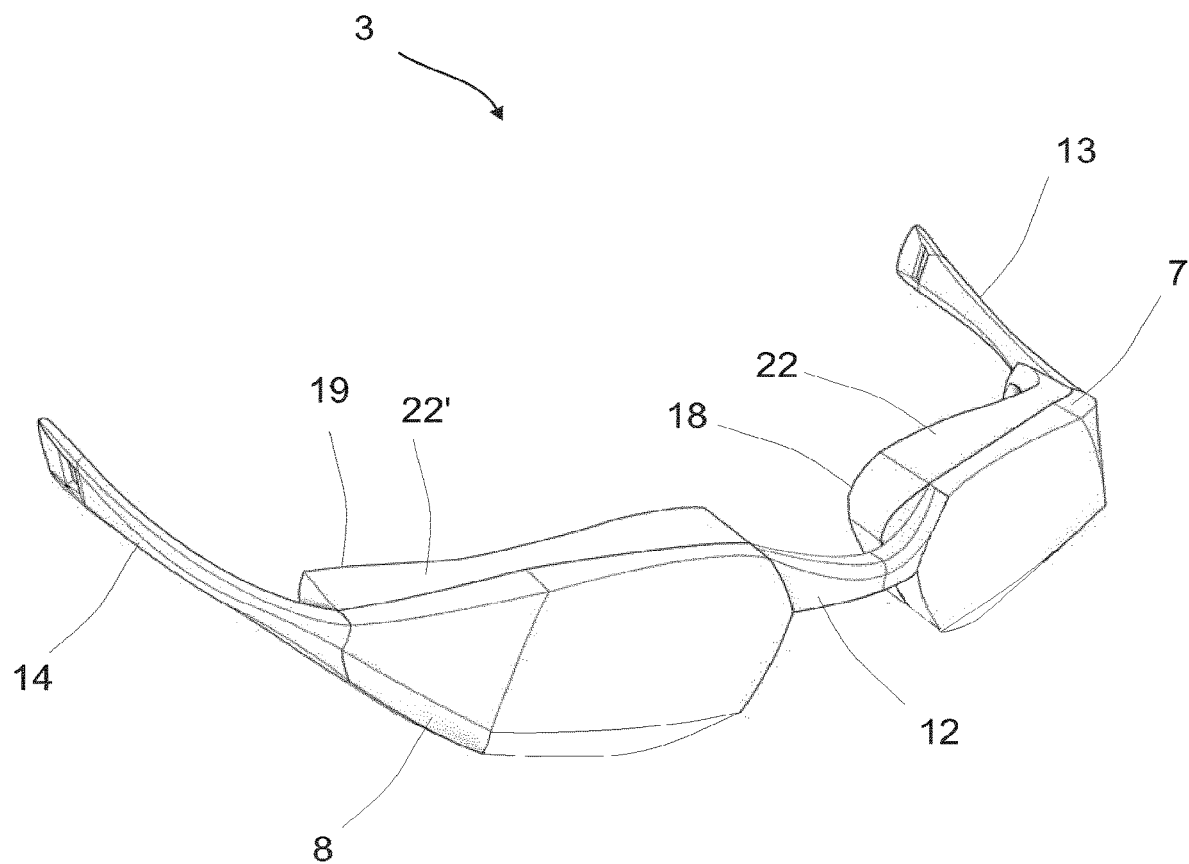
FIG. 7 shows a pair of assembled user-customised goggles, seen in perspective.

In FIG. 7, a pair of assembled user-customised goggles 3 is seen in perspective. For similar features as shown in the previous Figs., similar reference numbers have been used.

The invention claimed is:

1. User-customized goggles, the user-customized goggles comprising:
    a user-contacting part; and
    a goggle frame, said goggle frame having an interior side closest to a face of a wearer, and an exterior side opposite the interior side,
    wherein said user contacting part comprises a first surface of a user contacting structure, said first surface comprising a user contacting surface having a user-customized shape specifically reproducing a contour and dimensions of the face of the wearer determined from 3D-data defining the contour of the face of the wearer and defining dimensions of the face of the wearer at least in an area around the eyes of the wearer,
    and said user contacting structure having a second surface opposite said first surface, said second surface adapted to engage with the interior side of the glass or lens frame of the goggle frame so that a solid and leak free connection is provided between the second surface of the user contacting structure and the interior side of the goggle frame, and
    wherein said user contacting structure comprises an ocular support that is substantially cylindrical having said second surface adapted to engage with the interior side of the goggle frame, and said first surface comprising said user contacting surface having the user-customized shape specifically reproducing the contour and the dimensions of the face of the wearer, said first and second surfaces separated by a separation length that varies around a circumference of the user contacting structure, said user contacting structure defining an inner opening through which the wearer can see when wearing the user-customized goggles; and
    wherein the user contacting surface is fabricated on said user contacting part, said user contacting surface having the user-customized shape specifically reproducing the contour and dimensions of the face of the wearer based on structure data, said structure-data generated by the 3D-data and identifying contact areas on the user contacting surface of the face of the wearer from the 3D-data, said structure-data provided to a production device for producing at least the user contacting part of the goggles, wherein:

said contact areas are identified by analyzing vectors at points around the wearer's eyes, the points around the wearer's eyes including inner eye corners and outer eye corners, said vectors moving away from the inner and outer eye corners in horizontal and vertical directions, and points between the inner and outer eye corners having vectors in the horizontal and vertical directions, and angles of the vectors relative to the face at each of the points are determined, and vectors that reach a predefined angle at each of the points relative to the face identify the contact areas.

2. The user-customized goggles according to claim 1, wherein the structure data further comprises the separation length that separates said first and second surfaces of the user contacting structure.

3. The user-customized goggles according to claim 1, wherein the user-customized goggles are swimming goggles.

4. The user-customized goggles according to claim 1, wherein said user-customized goggles further comprise a heating means.

5. The user-customized goggles according to claim 1, wherein the 3D-data is produced at least in part from a plurality of 2D-images of the face of the wearer, where the 2D-images define the dimensions of the face of the user wearer at least in the area around the eyes of the wearer.

6. The user-customized goggles of claim 1, wherein the separation length is 4 mm or greater at some locations around the circumference of the user contacting structure.

7. The user-customized goggles of claim 1, wherein the user-customized goggles are adapted to encircle at least one of the eyes of the wearer.

8. The user-customized goggles of claim 1, wherein the user-customized goggles are adapted to encircle both of eyes of the wearer together.

9. The user-customized goggles of claim 1, wherein the user-customized goggles comprise ski goggles, (fire)-fighting goggles, or gasmasks.

10. User-customized goggles comprising:

a goggle frame, said goggle frame having an interior side closest to a face of a wearer, and an exterior side opposite the interior side; and a user-contacting part, wherein said user contacting part comprises a first surface, said first surface having a user-customized shape specifically reproducing a contour and dimensions of the face of the wearer determined from data defining the contour of the face of the wearer and defining dimensions of the face of the wearer at least in an area around one or both eyes of the wearer, and said user contacting part having a second surface opposite said first surface, said second surface adapted to engage with the interior side of the goggle frame so that a solid and leak free connection is provided between the second surface of the user contacting part and the interior side of the goggle frame, and wherein said first and second surfaces of the user contacting part are separated by a separation length that varies around a circumference of the user contacting part, said user contacting part defining an inner opening through which the wearer can see when wearing the user-customized goggles; and wherein said data defining the contour of the face of the wearer and defining dimensions of the face of the wearer at least in the area around one or both eyes of the wearer is used to identify contact areas of the first surface of the user contacting part by analyzing vectors at points around one or both of the wearer's eyes, the points around one or both of the wearer's eyes including inner eye corners and outer eye corners, said vectors moving away from the inner and outer eye corners in horizontal and vertical directions, and points between the inner and outer eye corners having vectors in the horizontal and vertical directions, and angles of the vectors relative to the face of the wearer at each of the points are determined, and vectors that reach a predefined angle at each of the points relative to the face identify the contact areas.

* * * * *

UNITED STATES PATENT AND TRADEMARK OFFICE
CERTIFICATE OF CORRECTION

| | | |
|---|---|---|
| PATENT NO. | : 12,193,975 B2 | Page 1 of 1 |
| APPLICATION NO. | : 18/510057 | |
| DATED | : January 14, 2025 | |
| INVENTOR(S) | : Bo Haaber | |

It is certified that error appears in the above-identified patent and that said Letters Patent is hereby corrected as shown below:

In the Claims

Column 11, Line 34-35:
In Claim 5, delete "user wearer" and insert -- wearer --.

Column 11, Line 39:
In Claim 7, delete "googles" and insert -- goggles --.

Signed and Sealed this
Twenty-fifth Day of March, 2025

Coke Morgan Stewart
*Acting Director of the United States Patent and Trademark Office*